United States Patent
Li

(10) Patent No.: US 10,441,628 B2
(45) Date of Patent: Oct. 15, 2019

(54) HIGH ACTIVITY TUMOUR INHIBITOR AND PREPARATION METHOD AND USE THEREOF

(71) Applicant: BAO KANG BIOMEDICAL HEALTHCARE INC, Shanghai (CN)

(72) Inventor: Kangshan Li, Shanghai (CN)

(73) Assignee: BAO KANG BIOMEDICAL HEALTHCARE INC, Shanghai (CN)

( * ) Notice: Subject to any disclaimer, the term of this patent is extended or adjusted under 35 U.S.C. 154(b) by 0 days.

(21) Appl. No.: 15/519,753

(22) PCT Filed: Oct. 15, 2015

(86) PCT No.: PCT/CN2015/092021
§ 371 (c)(1),
(2) Date: Jul. 19, 2017

(87) PCT Pub. No.: WO2016/058547
PCT Pub. Date: Apr. 21, 2016

(65) Prior Publication Data
US 2017/0319648 A1  Nov. 9, 2017

(30) Foreign Application Priority Data

Oct. 17, 2014  (CN) .......................... 2014 1 0555112

(51) Int. Cl.
| | | |
|---|---|---|
| A61K 38/10 | (2006.01) | |
| C07K 7/08 | (2006.01) | |
| A61K 38/16 | (2006.01) | |
| C07K 14/00 | (2006.01) | |

(52) U.S. Cl.
CPC .............. *A61K 38/10* (2013.01); *A61K 38/16* (2013.01); *C07K 7/08* (2013.01); *C07K 14/00* (2013.01)

(58) Field of Classification Search
CPC .................................. A61K 38/10; C07K 7/08
See application file for complete search history.

(56) References Cited

FOREIGN PATENT DOCUMENTS

| CN | 101918034 | 12/2010 | | |
|---|---|---|---|---|
| CN | 102015758 | 4/2011 | | |
| CN | 102136042 | 7/2011 | | |
| CN | 104558119 | 4/2015 | | |
| CN | 104558119 A | * 4/2015 | ............... | C07K 7/06 |
| EP | 2868326 | 5/2015 | | |
| WO | 2015022283 | 2/2015 | | |
| WO | WO-2015055148 A1 | * 4/2015 | ............... | C07K 7/06 |

OTHER PUBLICATIONS

International Search Report for international appl. No. PCT/CN2015/092021, dated Jan. 18, 2016 (4 pages, including English translation).
A.W. White et al., "Protein-protein interactions as targets for small-molecule therapeutics in cancer," Expert Reviews in Molecular Medicine, vol. 10, No. 8 (2008), 14 pages.
Sang Hoon Joo, Cyclic peptides as therapeutic agents and biochemical tools, Biomol Ther 20(1), 19-26 (2012).
J. Hau et al., "The TEAD4-YAP/TAZ Protein-Protein Interaction: Expected Similarities and Unexpected Differences," ChemBioChem, vol. 14 (2013), p. 1218-1225.
Z. Zhang et al., "Structure-Based Design and Synthesis of Potent Cyclic Peptides Inhibiting the YAP-TEAD Protein-Protein Interaction," ACS Medicinal Chemistry Letters, vol. 5 (2014), p. 993-998.
Search Report issued for Chinese patent appl. No. 2014105551462, dated Feb. 15, 2017 (3 pages, including English translation).
Search Report issued for European patent appl. No. 14853519.8, dated May 26, 2017 (13 pages).
Peter M. Fischer, Cellular Delivery of Impermeable Effector Molecules in the Form of Conjugates with Peptides Capable of Mediating Membrane Translocation, Nov./Dec. 2001 vol. 12, No. 6, Bioconjugate Chemistry.
Google Translation of CN102136042 A (previously cited), accessed on Jun. 1, 2017.
Herman Berendsen, A glimpse of the Holy Grail, Science, Oct. 23, 1998, 282, 5389, p. 642.
Maulik V. Trivedi, The role of thiols and disulfides in protein chemical and physical stability, Curr Protein Pept Sci. Dec. 2009; 10(6): 614-625.
JA Parsons, Peptide Hormones, pp. 1-8, 1976.
Sigma, Custom Peptide Synthesis, Designing Custom peptides, pp. 1-2, 2004.
Donald Voet, Biochemistry, 1995, Section 9.4, pp. 235-241.
Bradley, Limits of Cooperativity in a structurally modular protein: response of the Notch Ankyrin Domain to Analogous Alanine substitutions in Each repeat, JMB, 2002, 324 pp. 373-386.
J. J. Tentler et al., "Patient-derived tumour xenografts as models for oncology drug development," Nat Rev Clin Oncol, vol. 9, No. 6 (2012), p. 338-350.
International Search Report for international application No. PCT/CN2014/088876, dated Jan. 16, 2015 (4 pages, including English translation).

(Continued)

*Primary Examiner* — Matthew P Coughlin
(74) *Attorney, Agent, or Firm* — Hamre, Schumann, Mueller & Larson, P.C.

(57) ABSTRACT

Provided in the present invention are a YAP protein inhibiting polypeptide and application thereof. In particular, the present invention obtains a key binding site of YAP protein and TEAD, screens a polypeptide with best YAP inhibitory activity and modifies the polypeptide, such as adding a disulfide linkage, replacing an amino acid, removing and/or adding (for example, adding a cell-penetrating element), and finally screens and verifies the obtaining of a series of polypeptides with YAP protein activity inhibiting effect and good stability. Experiments show that the polypeptide of the present invention can effectively inhibit the binding activity between YAP protein and TEAD, thus providing good therapeutic effect on digestive tract tumors (especially liver cancer).

4 Claims, 3 Drawing Sheets
Specification includes a Sequence Listing.

(56) References Cited

OTHER PUBLICATIONS

Partial Supplementary European Search Report issued for European Patent Application No. 15850708.7, dated May 8, 2018, 18 pages.
Y. Liu-Chittenden et al., "Genetic and pharmacological disruption of the TEAD-YAP complex suppresses the oncogenic activity of YAP," Genes & Development, vol. 26, No. 12, pp. 1300-1305 (Jun. 7, 2012).
Li, Ze et al., "Structural insights into the YAP and TEAD Complex," Genes & Development, vol. 24, No. 3, pp. 235-240 (Feb. 1, 2010).
Extended European Search Report issued for European Patent Application No. 15850708.7, dated Sep. 12, 2018, 21 pages.
Abstract of Kabanov, A. V. et al., "Fatty Acylation of Proteins for Translocation Across Cell Membranes," Biomedical SCL, London, GB, vol. 1, No. 1, pp. 33-36 (Jan. 1, 1990); 1 page.
Utsumi, T. et al., "Preparation and Characterization of Liposomal-Lipophilic Tumor Necrosis Factor," Cancer Research, American Association for Cancer Research, US, vol. 51, No. 13, pp. 3362-3366 (Jul. 1, 1991).
Torchilin, V. P. et al, "Incorporation of hydrophilic protein modified with hydrophobic agent into liposome membrane," Biochimica Et Biophysica Acta (BBA) Biomembranes, Elsevier, Amsterdam NL, vol. 602, No. 3, pp. 511-521 (Nov. 18, 1980).

* cited by examiner

HIGH ACTIVITY TUMOUR INHIBITOR AND PREPARATION METHOD AND USE THEREOF

TECHNICAL FIELD

The present invention relates to tumor therapy field. In particular, the present invention relates to novel YAP protein inhibiting polypeptides for treating digestive tract tumors.

TECHNICAL BACKGROUND

Liver cancer is one of the cancers with high incidence rate in the world, particularly in China. Due to the high incidence of viral hepatitis, main prognosis of chronic viral hepatitis is to develop into cirrhosis or even liver cancer. There is no technology and method available to cure liver cancer at the present medical levels. Surgical removal of tumor locally is a primary method of treatment, and very few patients can receive a liver resection and a liver transplantation. The recurrence rate of liver cancer after surgery is extremely high, since no method can eliminate the potential lesions completely. According to statistics, the recurrence rate is about 40% in 3 years, and more than 90% in 7 years.

In recent years, a variety of oncotherapy medicines and methods have been developed, but efficacy is still not ideal for malignant tumors, such as liver cancer.

Therefore, there is an urgent need in developing an effective method for treating digestive tract tumors, especially liver cancer.

SUMMARY OF INVENTION

The present invention provides an innovative medicine for treating digestive tract tumors. The medicine is a polypeptide which can extremely effectively inhibit YAP protein, thus inhibiting tumors.

The present invention provides a YAP protein inhibiting polypeptide and its use for treating digestive tract tumors, especially liver cancer.

In the first aspect, the present invention provides an isolated polypeptide which has a structure as shown in formula A:

$$X_0\text{-}Y_1\text{-}Y_2\text{-}Y_3\text{-}Y_4\text{-}Y_5\text{-}Y_6\text{-}X_A\text{-}X_E\text{-}X_F \quad (A)$$

wherein, $X_0$ or $X_A$ is not present, or is 1, 2, 3, or 4 amino acid residues;

$Y_1$ is AP, VP, or not present;

$Y_2$ is $X_1\text{-}X_2\text{-}X_{2a}$, wherein $X_1$ is selected from M, F, C or Hcy; $X_2$ is an arbitrary amino acid residue (preferably $X_2$ is C, Hcy, L, M, or F); and $X_{2a}$ is L, Nle, C, Hcy, K or R;

$Y_3$ is $X_{3a}\text{-}X_3\text{-}X_4$, wherein $X_{3a}$ is alkaline amino acid R or K; $X_3$ is an arbitrary amino acid (preferably $X_3$ is K, R, Hcy, C, Orn or Dab); and $X_4$ is an arbitrary amino acid (preferably $X_4$ is L, Nle, Hcy, or C), and at least one amino acid of $Y_3$ is Hcy or C;

$Y_4$ is P;

$Y_5$ is $X_5$, and $X_5$ is an arbitrary amino acid (preferably $X_5$ is A, D, or E);

$Y_6$ is S-$X_{6a}$-$X_6$, wherein $X_{6a}$ is F, C, or Hcy; and $X_6$ is an arbitrary amino acid residue (preferably $X_6$ is C, Hcy, F, K or R);

$Y_7$ is $X_7\text{-}P\text{-}X_{7a}$, wherein $X_7$ is an arbitrary amino acid residue (preferably $X_7$ is C, Hcy, K, R or P); and $X_{7a}$ is C, Hcy or P;

$X_E$ is not present or is a cell-penetrating element;

$X_F$ is not present or K; and the polypeptide exhibits an inhibitory activity on Yes-associated protein (YAP).

In another preferred embodiment, the cell-penetrating element has a terminal residue of K (lys).

In another preferred embodiment, $X_A$ is K.

In another preferred embodiment, $X_F$ is not present and $X_A$ is K.

In another preferred embodiment, $X_A$ is not present and $X_E$ is K.

In another preferred embodiment, at least one amino acid of $Y_2$ and/or $Y_3$ is Hcy or C; and at least one amino acid of $Y_6$ or $Y_7$ is Hcy or C.

In another preferred embodiment, at least one amino acid of $Y_2$ is Hcy or C.

In another preferred embodiment, $X_{3a}$ or $X_3$ of $Y_3$ is Hcy or C.

In another preferred embodiment, $Y_5$ (or $X_5$) is Hcy or C, or an arbitrary amino acid residue.

In another preferred embodiment, $X_{6a}$ or $X_6$ of $Y_6$ is Hcy or C.

In another preferred embodiment, $X_7$ or $X_{7a}$ of $Y_7$ is Hcy or C.

In another preferred embodiment, $X_E$ is a cell-penetrating element.

In another preferred embodiment, at least one pair of disulfide linkage is formed, optionally between residues of $X_1$, $X_2$, $X_{2a}$, $X_3$, $X_{3a}$, $X_5$, $X_6$, $X_{6a}$, $X_7$ and $X_{7a}$.

In another preferred embodiment, one or two pairs of disulfide linkages are formed, optionally between residues of $X_1$, $X_2$, $X_{2a}$, $X_3$, $X_{3a}$, $X_5$, $X_6$, $X_{6a}$, $X_7$ and $X_{7a}$.

In another preferred embodiment, the disulfide linkage is formed between one amino acid selected from $X_1$, $X_2$, $X_{2a}$, $X_3$ and $X_{3a}$ and one amino acid selected from $X_5$, $X_6$, $X_{6a}$, $X_7$ and $X_{7a}$.

In another preferred embodiment, the disulfide linkage is formed between $X_1$ and $X_{6a}$, between $X_2$ and $X_6$, between $X_{2a}$ and $X_7$, between $X_{3a}$ and $X_7$, or between $X_3$ and $X_{7a}$.

In another preferred embodiment, the disulfide linkage is formed between $X_2$ and $X_6$, between $X_5$ and $X_7$, between $X_2$ and $X_7$, or between $X_5$ and $X_6$.

In the second aspect, the present invention provides an isolated polypeptide which has a structure as shown in formula V:

$$X_0\text{-}Z\text{-}X_A\text{-}X_E\text{-}X_F \quad (V)$$

wherein, $X_0$ or $X_A$ is not present, or is 1, 2, 3, or 4 amino acid residues;

$X_E$ is not present or is a cell-penetrating element;

$X_F$ is not present or K;

Z is a YAP inhibiting polypeptide having an introduced intra-chain disulfide linkage, and Z has a basic sequence as shown in formula Va after the corresponding amino acids for forming intra-chain disulfide linkages are removed:

$$\text{Z1-Z2-Z3-Z4-Z5-Z6-Z7-Z8-Z9-Z10-Z11-Z12-Z13-Z14-Z15-Z16} \quad \text{Formula Va}$$

wherein,

Z1 is V, A, or not present;

Z2 is P, A, or not present;

Z3 is M, F, L, or chlorophenylalanine;

Z4 is R, K, A, or not present;

Z5 is L, Nle, A, or not present;

Z6 is R, or K;

Z7 is K, R, Orn, Dab, or A;

Z8 is L, or Nle;

Z9 is P;
Z10 is any natural or unnatural amino acid, and preferably D, A, V, L, I or E;
Z11 is S, or T;
Z12 is F, L, or chlorophenylalanine;
Z13 is F, L, chlorophenylalanine or not present;
Z14 is K, R, A, or not present;
Z15 is P, A, or not present;
Z16 is P, A, or not present;
wherein, the first amino acid B1 of disulfide linkage is located between any two amino acids in a first segment formed by Z1 to Z8 in the basic sequence or is located before the first amino acid of the first segment, and the second amino acid B2 of disulfide linkage is located between any two amino acids in a second segment formed by Z9 to Z16 in the basic sequence or is located after the last amino acid of the second segment.

In another preferred embodiment, Z4 and Z5 are not both nonexistence at the same time.

In another preferred embodiment, the first amino acid B1 is located between Z2 and Z3, between Z3 and Z4, between Z3 and Z5 (when Z4 is not present), between Z4 and Z5, or between Z7 and Z8, and/or
the second amino acid B2 is located between Z11 and Z12, between Z12 and Z13, between Z13 and Z14, after Z14 (when Z15 and Z16 is not present), after Z15 (when Z16 is not present), or after Z16.

In another preferred embodiment, the sequence difference between the sequence shown in Z3 to Z13 in formula Va and the sequence represented by positions 3 to 15 in SEQ ID NO.: 1 is ≤1, ≤2, ≤3, ≤4, or ≤5 amino acids, and preferably or amino acids.

Please note that the sequence consisting of positions 3 to15 in SEQ ID NO.: 1 or the corresponding Z3 to Z13 is a core sequence.

In another preferred embodiment, there are 3-14 (preferably 4-12, more preferably 4-10, and most preferably 7, 8, or 9) amino acids between the first amino acid B1 and the second amino acid B2.

In another preferred embodiment, the first amino acid B1 and second amino acid B2 are independently selected from Hcy or C.

In another preferred embodiment, one or more amino acids selected from the group consisting of Z1, Z2, and Z14-Z16 are not present.

In another preferred embodiment, the arbitrary amino acid includes natural or unnatural amino acid.

In another preferred embodiment, a distance between the disulfide linkages is 4, 5, 6, 7, 8, 9, or 10 amino acids, wherein the amino acids forming the disulfide linkage are excluded. Preferably, the distance is 5, 6, 7, 8, or 9 amino acids.

In another preferred embodiment, the number of the disulfide linkages is one pair.

In another preferred embodiment, the polypeptide of formula A or formula V contains at least one unnatural amino acid.

In another preferred embodiment, the identity (or homology) between the polypeptide of formula A or formula V and SEQ ID NO.: 1 is ≥50%, ≥60%, ≥70%, ≥80%, or ≥90%.

In another preferred embodiment, the polypeptide of formula A or formula V retains ≥50%, ≥60%, ≥70%, ≥80%, ≥90%, or ≥100% (for example 80-500%, and preferably 100-400%) biological activity of SEQ ID NO.: 1.

In another preferred embodiment, the biological activity refers to the activity of inhibiting a binding between YAP and TEAD.

In another preferred embodiment, the polypeptide has a structure as shown in formula I:

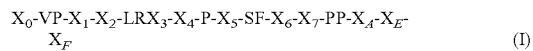

wherein the polypeptide has the following characteristics:
(a) $X_0$ or $X_A$ is not present, or is 1, 2, 3, or 4 amino acid residues;
(b) $X_1$ is selected from M or F;
(c) each of $X_2$, $X_5$, $X_6$ or $X_7$ independently is an arbitrary amino acid residue, and there is at least one pair of disulfide linkage which is formed optionally among $X_2$, $X_5$, $X_6$ and $X_7$;
(d) $X_3$ or $X_4$ is an arbitrary amino acid; and
(e) $X_E$ is not present or a cell-penetrating element;
(f) $X_F$ is not present or K;
and the polypeptide exhibits an inhibitory activity on Yes-associated protein (YAP).

In another preferred embodiment, the disulfide linkage is formed between $X_2$ and $X_6$ and/or the disulfide linkage is formed between $X_5$ and $X_7$.

In another preferred embodiment, $X_3$ is K or a similar amino acid thereof which is preferably selected from K, Orn, or Dab.

In another preferred embodiment, $X_4$ is L or a similar amino acid thereof which is preferably selected from L, or Nle.

In another preferred embodiment, the cell-penetrating element has a length of 4-20 amino acids, and preferably 5-15 amino acids.

In another preferred embodiment, the YAP-inhibitive activity includes inhibition of binding between YAP and TEAD protein.

In another preferred embodiment, the polypeptide inhibits the binding between interface 3 of YAP (aa86-100) and TEAD protein.

In another preferred embodiment, the polypeptide has a structure as shown in formula II:

In another preferred embodiment, the amino acid residues which form a disulfide linkage at $X_2$, $X_5$, $X_6$ and $X_7$ are independently selected from Cys or Hcy.

In another preferred embodiment, the disulfide linkages are formed by Cys-Hcy, or Cys-Cys.

In another preferred embodiment, each of $X_2$, $X_5$, $X_6$ and $X_7$ is same or different.

In another preferred embodiment, $X_2$ is Hcy and/or $X_6$ is Cys.

In another preferred embodiment, $X_E$ is selected from any of the sequences as shown in SEQ ID NOs.: 13, 14 and 15 (RRMKWKK/GRKKRRQRRR/KKKRKV).

In another preferred embodiment, the sequence of the polypeptide is shown as any of sequences SEQ ID NOs.: 1-12, and 22-37.

In another preferred embodiment, the basic sequence of Z is from mammal YAP, and preferably from rodent or human YAP.

In the third aspect, the present invention provides an isolated nucleic acid encoding the polypeptide as described herein.

In the fourth aspect, the present invention provides a pharmaceutical composition comprising the polypeptide according to the first or the second aspect of the present invention or the modified polypeptide according to the eighth aspect of the present invention or a pharmaceutically acceptable salt thereof as an active ingredient.

In another preferred embodiment, the pharmaceutical composition is a liposome preparation.

In another preferred embodiment, the pharmaceutical composition (such as a liposome preparation) comprises the polypeptide according to the first or the second aspect of the present invention or the modified polypeptide according to the eighth aspect of the present invention.

In another preferred embodiment, the pharmaceutical composition is administered by using an administration manner selected from the group consisting of: intravenous, intratumoral, oral, intracavitary, subcutaneous administration and administration via hepatic artery (such as injection, or drip).

In another preferred embodiment, the pharmaceutical composition has a formulation selected from the group consisting of: tablet, capsule, injection, granule, spray, and lyophilized powder.

In another preferred embodiment, the formulation of pharmaceutical composition is injection.

In another preferred embodiment, the polypeptide is administered to a mammal at a dose of 0.01-20 mg/kg weight (each time or each day).

In the fifth aspect, the present invention provides a use of the polypeptide in the first or the second aspect of the present invention or the modified polypeptide according to the eighth aspect of the present invention, wherein the polypeptide is used for preparing a pharmaceutical composition for treating a tumor, a composition for inhibiting tumor cell growth, and/or a pharmaceutical composition for inhibiting YAP activity.

In another preferred embodiment, the tumor or tumor cell has YAP overexpression.

In another preferred embodiment, the "YAP overexpression" means the ratio of expression quantity Ec of YAP in tumor tissue to expression quantity En of YAP in para-carcinoma tissue (or normal tissue) (Ec/En) is ≥2, ≥3, ≥5 (such as 2-20).

In another preferred embodiment, the expression quantity includes the quantity of protein expression or the quantity of mRNA expression.

In another preferred embodiment, the tumor with YAP overexpression includes digestive tract tumor.

In the seventh aspect, the present invention provides a method for treating a tumor, comprising a step of:

administering a safe and effective amount of the polypeptide of the present invention or a pharmaceutical composition of the present invention to a subject in need.

In another preferred embodiment, the subject in need refers to a subject suffered from a tumor with a YAP overexpression.

In another preferred embodiment, the tumor is a tumor with a YAP overexpression.

In another preferred embodiment, the tumor includes digestive tract tumor.

In another preferred embodiment, the digestive tract tumor includes liver cancer, gastric cancer, colorectal cancer, gallbladder cancer, and pancreatic cancer.

In another preferred embodiment, the subject is human.

In the eighth aspect, the present invention provides a modified polypeptide which is formed by acylation of a polypeptide in the first or second aspect of the present invention.

In another preferred embodiment, the modified polypeptide is formed by an acylation reaction with a $C_{10}$-$C_{24}$, preferably $C_{12}$-$C_{20}$, and more preferably $C_{16}$-$C_{18}$ acylation agent.

In another preferred embodiment, the modified polypeptide has a structure as shown in formula B:

$$P_0\text{-}X_G \qquad \text{formula B}$$

wherein, $X_G$ is a $C_{10}$-$C_{24}$ acyl, and P0 is a polypeptide of formula A or V.

In another preferred embodiment, $X_G$ links to a terminal (such as C-terminal) of $P_0$ or in the middle of P0.

In another preferred embodiment, $X_G$ links to a side $-NH_2$ of K at the terminal of $P_0$.

In another preferred embodiment, the modified polypeptide has a structure as follows:

$$A\text{-}X_G; \text{ or} \qquad \text{Formula}$$

$$V\text{-}X_G. \qquad \text{Formula}$$

In another preferred embodiment, the acyl is a saturated or unsaturated and/or substituted or unsubstituted acyl group.

In the ninth aspect, the present invention provides a use of the polypeptide in the first or second aspect of the present invention or the modified polypeptide according to the eighth aspect of the present invention, wherein the polypeptide is used for preparing a pharmaceutical composition for treating a tumor, a composition for inhibiting tumor cell growth, and/or a pharmaceutical composition for inhibiting YAP activity.

In the tenth aspect, the present invention provides a method for modifying a YAP inhibitory polypeptide, which comprises steps of:

(i) reacting a polypeptide in the first or second aspect of the present invention with an acylation agent under a suitable condition, thereby forming an acylated and modified YAP inhibitory polypeptide.

In another preferred embodiment, the acylation agent comprises a $C_{10}$-$C_{24}$, preferably $C_{12}$-$C_{20}$, and more preferably $C_{16}$-$C_{18}$ acylation agent. Preferably, it is acyl halide.

In another preferred embodiment, the modification method further comprises a step of:

(ii) the acylated YAP inhibitory polypeptide obtained in (i) is made into a liposome form.

It should be understood that in the present invention, the technical features specifically described above and below (such as the Examples) can be combined with each other, thereby constituting a new or preferred technical solution, which needs not be described one by one, due to space limitations.

MODES FOR CARRYING OUT THE PRESENT INVENTION

Figure 1:
FIG. 1 shows a schematic diagram of method for screening polypeptides in the present invention, i.e., TR-FRET test.
Figure 2:
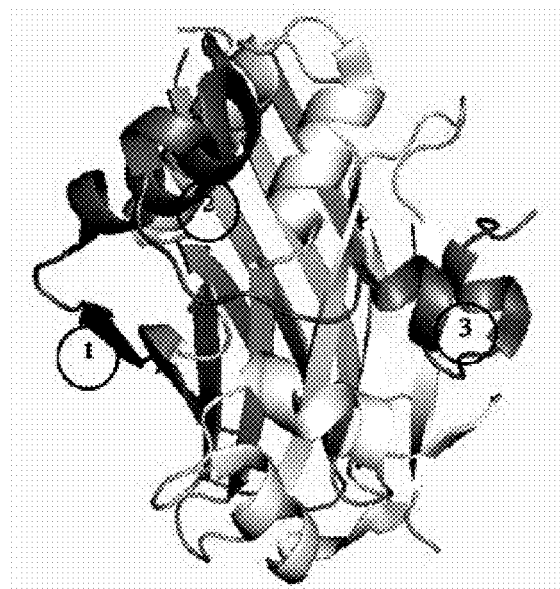
FIG. 2 shows a schematic diagram of YAP-TEAD binding, wherein ③ is the site for which the polypeptide of the present invention competes with YAP for binding to TEAD.
Figure 3:
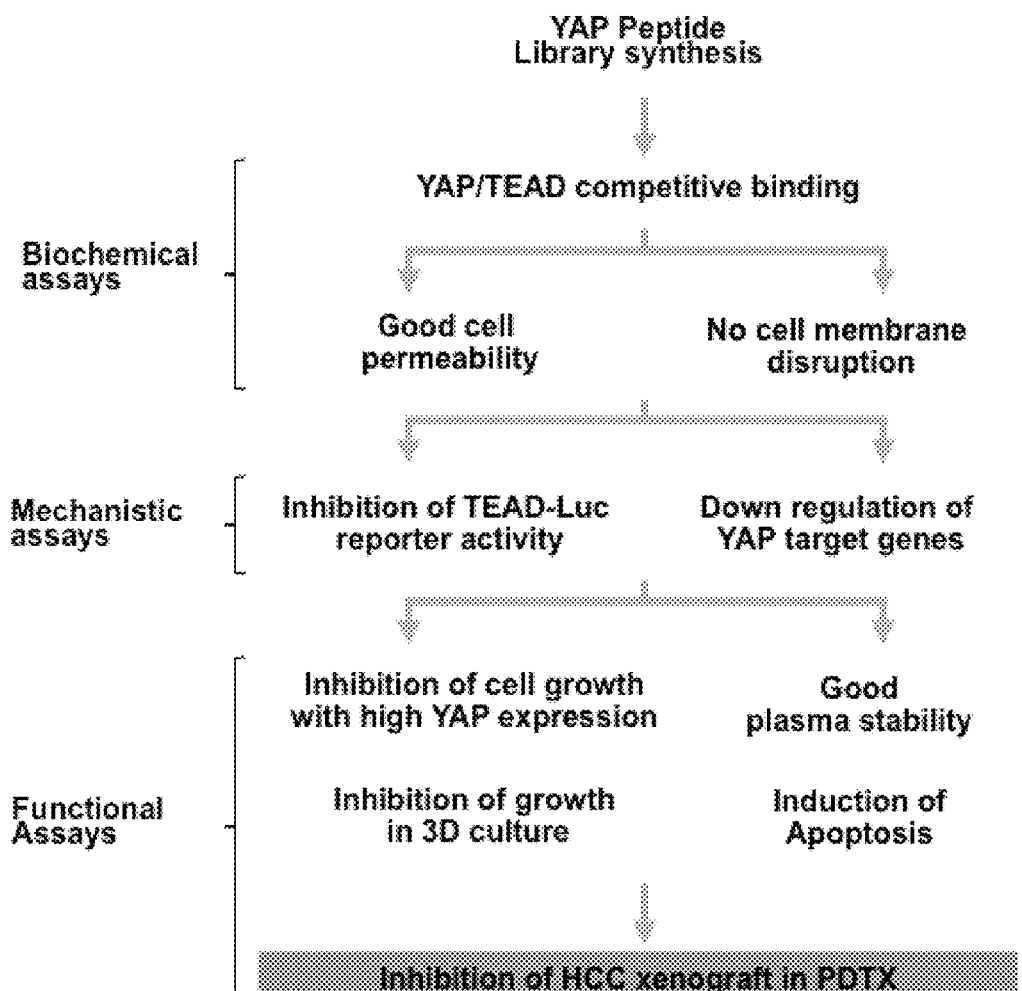
FIG. 3 shows a screening process of the polypeptide of the present invention.

After extensive and intensive study, the inventor firstly constructed a peptide library using arrangement of YAP protein, and prepared several YAP inhibiting polypeptides after screening. Such YAP inhibitory polypeptides can effectively inhibit the interaction between YAP and TEAD. In particular, by integrating several different technologies including technology for producing protein and peptide, technology of anastomosed peptide, and technology of cell-penetrating element, the inventor successfully developed a stable YAP protein inhibiting polypeptide which can effectively penetrate cells and significantly inhibit YAP-TEAD protein complexes in cells. Experiments have shown that the polypeptides of the present invention have a good drug stability, a good cell-penetrating ability in vivo, a half life of more than 24 hours in the blood, a cell invasion rate of more than 80%, and a $EC_{50}$ at nano-mole order for inhibiting the binding between YAP and TEAD.

The inventor has also conducted numerous reconstructions and derivation based on the sequence of SEQ ID NO.: 1 which was obtained by screening. The experiments have shown that, after certain amino acid (Hcy or Cys) for forming a disulfide linkage is incorporated at specific position by insertion or replacement, and/or some amino acid residues in the core sequence (Z) is replaced to a certain extent, the polypeptide of the present invention have better stability. Moreover, after adding a cell-penetrating peptide fragment at N-terminus of these polypeptides, one can obtain a peptide having good (even superior) inhibitive activity of inhibiting YAP protein.

In addition, the present inventors have further modified and improved the protein obtained by screening. In particular, the present inventors have linked an acyl group (e.g., a $C_{10}$-$C_{24}$ acyl halide) at the C-terminus of the polypeptide of the present invention with a membrane penetrating fragment, thereby greatly improving the potency of the polypeptide of invention and effectively enhancing the cell proliferation inhibition effect after it is further made into a liposome preparation.

YAP Protein

YAP is an important cancer gene in the Hippo signaling pathway, which affects growth of tumor cells. The human gene of Yes-associated protein 1 is available in public databases (such as Protein GenBank) or literatures. The ID of gene sequence of Yes-associated protein 1 is 10413; and protein sequence thereof is AAH38235.1.

Previous studies have shown that YAP protein is significantly enriched in human hepatocellular carcinoma and over expressed in various solid tumors, and more than 60% in liver cancer. The expression degree is closely related to the clinical prognosis in hepatocellular carcinoma.

In addition, it is deemed that YAP proteins are highly expressed in various solid tumors of the digestive system, such as gastric cancer, colorectal cancer, gallbladder cancer, pancreatic cancer, and so on. Therefore, YAP is considered to be a potential cancer gene in gastrointestinal cancer. As used herein, said "high expression (or overexpression) of YAP" means the ratio of expression quantity Ec of YAP in tumor tissue to expression quantity En of YAP in para-carcinoma tissue (or normal tissue) (Ec/En) is ≥2, ≥3, ≥5 (such as 2-20). Generally, the expression level of YAP protein can be obtained by conventional methods.

YAP-TEAD Complexes

YAP and TEAD are major molecules that control cell growth in the nucleus of liver cells. The interaction between YAP-TEAD activates growth genes, thus promoting division and growth of cells.

The inventor has constructed various phage peptide libraries using technology of arrangement of YAP protein. Based on a lot of screening experiments and for the first time, interface 3 (AA86-100) of YAP was confirmed to be the most important interface affecting the binding between YAP and TEAD, and other interfaces can only play a limited role in the binding between YAP and TEAD.

The polypeptide of the present invention can effectively bind with TEAD protein, thus inhibiting the binding of YAP-TEAD.

Patient-Derived Tumor Xenograft Animal Model (Patient-Derived Tumor Xenograft, PDTX)

Patient-derived tumor xenograft is the most advanced animal model. The obtained carcinoma tissue of patient is implanted into nude mice. The implanted tissue pieces can grow into carcinoma or solid tumor after special handling. Literatures show that, compared with the traditional cell lines animal model, xenograft animal model is closer to human cancer in pathology and structure of carcinoma tissue than and, therefore, has a very high value of translational medicine. For animal models of the present invention, please refer to "Patient-derived tumor xenografts as models for oncology drug development. Tentler et al, Nat Rev Clin Oncol; 9:338-350 (2012)".

Active Polypeptides

In the present invention, the term "the polypeptide(s) of the present invention", "the small peptide(s) of the present invention", "YAP inhibiting peptide(s)" can be used interchangeably. All of them refer to the protein or polypeptide having amino acid sequence (formula I, formula A, formula V or formula Va) and exhibiting an activity of inhibiting YAP. In addition, said terms also comprise the variations which conform to formula I, formula A, formula V or formula Va and which exhibit an activity of inhibiting YAP. These variations include, but are not limited to, addition of one or more amino acids (typically less than 5, preferably less than 3, more preferably less than 2) at N-terminus. For example, the protein function is usually unchanged when an amino acids is substituted by a similar or analogous one. The addition of one or several amino acids at N-terminus generally will not change the structure and function of protein. In addition, the terms also include the monomer and polymer of the polypeptide of the present invention.

The present invention further includes the active fragments, derivatives and analogs of the polypeptide of the present invention. As used herein, the terms "fragments", "derivatives" and "analogs" refer to the polypeptides basically maintaining the function or activity of inhibiting YAP protein. The polypeptide fragments, derivatives or analogs of the present invention may be (i) a polypeptide with one or more conservative or non-conservative amino acid residues (preferably the conservative amino acid residues) being substituted, or (ii) a polypeptide having substituted group(s) in one or more amino acid residues, or (iii) a polypeptide formed by fusion of the polypeptide of the present invention with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or tag sequence, such as 6His. According to the subject application, these fragments, derivatives and analogs are within the scope commonly known by the skilled person.

A class of preferred active derivatives is the polypeptides formed by replacing at most 5, preferably at most 3, more preferably at most 2, most preferably 1 amino acid of the amino acid sequence represented by formula I with the amino acid having similar or analogous property. These conservative variant polypeptides are preferably formed by carrying out the amino acid replacement according to Table 1a.

TABLE 1a

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The invention also provides the analogues of the polypeptide of the present invention. These analogues can differ from the naturally occurring polypeptide of the present invention by amino acid sequence differences or by modifications that do not affect the sequence, or by both. Also included are analogues which include residues other than those naturally occurring L-amino acids (e.g., D-amino acids) or non-naturally occurring or synthetic amino acids (e.g., beta- or gamma-amino acids). For example, Cys can form a disulfide linkage with the non-natural Hcy. It is understood that, the polypeptides of the present invention is not limited to the representative polypeptides listed hereinabove.

Some of the commonly used non-natural amino acids are shown in the following table 1b.

TABLE 1b

| Designation | Abbreviation | Molecular formula | Molecular formula of residue |
|---|---|---|---|
| a-Aminobutyric acid | Abu | $C_4H_9NO_2$ | $C_{15}H_{13}NO$ |
| a,y-Diaminobutyric acid | Dab | $C_4H_{10}N_2O_2$ | $C_4H_8N_2O$ |
| Norleucine | Nle | $C_6H_{13}NO_2$ | $C_6H_{11}NO$ |
| Ornithine | Orn | $C_5H_{12}N_2O_2$ | $C_5H_{10}N_2O$ |
| Hydroxy-proline | Hyp | $C_5H_9NO_3$ | $C_5H_7NO_2$ |
| Homocysteine | Hcy(hC) | $C_4H_9NO_2S$ | $C_4H_7NOS$ |
| 6-Hydroxy-lysine | Hyl | $C_6H_{14}N_2O_3$ | $C_6H_{12}N_2O_2$ |
| Homoarginine | Har | $C_7H_{16}N_4O_2$ | $C_7H_{14}N_4O$ |
| Chlorophenylalanine | (Cl—)F | $C_9H_{10}ClNO_2$ | $C_9H_8ClNO$ |

Modification (usually do not change the primary structure) includes in vivo or in vitro chemical derivation of polypeptides, e.g., acetylation, or carboxylation. Also included is modification of glycosylation, e.g., the polypeptides made by subjecting to the glycosylation modification during its synthesis and processing or in the further processing steps. These modifications can be accompanied by exposing the polypeptide to enzymes which affect glycosylation (e.g., mammalian glycosylating or deglycosylating enzymes). Also included are sequences that have phosphorylated amino acid residues, e.g., phosphotyrosine, phosphoserine, phosphothronine, as well as sequences that have been modified to improve their resistance to proteolytic degradation or to optimize solubility properties. Preferably, it is a polypeptide having an enhanced solubility property after modification of acylation.

In a preferred embodiment, the present invention specifically provides a modified polypeptide modified by a $C_{10}$-$C_{24}$ acyl group, and a liposome preparation comprising the modified polypeptide of the present invention. It should be understood that there is no particular limitation on acyl groups useful in the present invention for acylation. It may be an acyl group having 10 to 24 carbon atoms including substituted or substituted and/or saturated or unsaturated acyl group. Preferably, the acyl groups having 10 to 24 carbon atoms useful in the present invention include those containing 10, 11, 12, 13, 14, 15, 16, 17, 18, 19, 20, 21, 22, 23, or 24 carbon atoms, such as acyl halides.

In a preferred embodiment, the polypeptide of the present invention has at least one internal disulfide linkage (an introduced intrachain disulfide linkage). Surprisingly, the presence of the internal disulfide linkage not only does not affect the inhibitory activity, but also is helpful to prolong half life and increase inhibitory activity. Generally, the disulfide linkage can be formed by using conventional methods in this field, such as combining the sulfydryl of homocysteine or cysteine under oxidative conditions. In the polypeptide of the present invention, the first amino acids B1 of the introduced internal disulfide linkage is located between any two amino acids in the first segment formed by Z1 to Z8 in the basic sequence or located before the first amino acid in the first segment, and the second amino acid B2 of the disulfide linkage is located between any two amino acids in the second segment formed by Z9 to Z16 in the basic sequence or located after the last amino acid of the second segment. Generally, there is at least one amino acid between the first amino acid B1 and the second amino acid B2 of the disulfide linkage, and any other reasonable distance which allows forming internal disulfide linkage can be accepted, for example, 3-12 amino acids. Preferred polypeptides of the present invention include polypeptides represented by SEQ ID NO.: 21-34, which are obtained via the modification of polypeptide represented by SEQ ID NO.: 1.

The polypeptides of the present invention can be used in a form of pharmaceutically or physiologically acceptable salt derived from acid or base. Such salts include, but are not limited to, the salts formed with the following acids: hydrochloric acid, hydrobromic acid, sulfuric acid, citric acid, tartaric acid, phosphoric acid, lactic acid, pyruvic acid, acetic acid, succinic acid, oxalic acid, fumaric acid, maleic acid, oxaloacetic acid, methanesulfonic acid, ethyl-sulfonic acid, benzene sulfonic acid, or isethionic acid. Other salts include salts formed with alkali metals or alkaline earth metals, such as sodium, potassium, calcium or magnesium, and esters, carbamate or other conventional "prodrug" forms.

Encoding Sequences

The present invention further relates to the polynucleotide encoding the polypeptide of the present invention. The polynucleotide of the present invention can be in a form of DNA or RNA. DNA can be the coding strand or the non-coding strand. The coding sequence encoding mature polypeptide can be identical to the coding sequence or can be a degenerate variant thereof. The whole length of the nucleotide sequence or the fragment thereof of the polypeptide of the present invention can be obtained via PCR amplification, recombinant method or artificial synthesis. Currently, the DNA sequence encoding the polypeptide (or fragment or derivative thereof) of the present invention can be prepared completely via chemical synthesis. Then the DNA sequence can be introduced into various existing DNA molecules (or such as vector) and cells known in the art.

The present invention also includes a vector containing the polynucleotide of the present invention, and a host cell engineered by the vector or the coding sequence of the polypeptide of the present invention.

In another aspect, the present invention further comprises a polyclonal antibody, monoclonal antibody or antibody fragment, especially the monoclonal antibody, having specificity to the polypeptide of the present invention.

Preparation Method

The polypeptide of the present invention can be recombinant or synthetic polypeptide. The polypeptide of the present invention can be a chemically synthesized or recombinant polypeptide. Accordingly, the polypeptide of the present invention can be artificially synthesized via a conventional method, or can be produced via a recombinant method.

One preferred method is to use liquid phase synthesis technique or solid phase synthesis technique, such as Boc solid phase process, Fmoc solid phase process, or combination thereof. By using the solid phase synthesis, a sample can rapidly be obtained, and one can select a suitable resin carrier and synthesis system according to the sequence feature of the target peptide. For example, the preferred solid phase carrier in Fmoc system can be, such as Wang resin linked to the C-terminal amino acid of the peptide, wherein the structure of the Wang resin is polystyrene, the arm between the resin and the amino acid is 4-alkoxy benzyl alcohol. The Wang resin is treated with 25% hexahydropyridine/dimethylfomamide for 20 minutes under room temperature to remove the Fmoc protective groups. Then the sequence is extended from the C-terminus to the N-terminus according to the predetermined amino acid sequence. After synthesis, trifluoroacetic acid containing 4% p-methylphenol is used to cleave the related peptide from the resin and the protective groups are removed. The resin can be filtered, and the crude peptide can be obtained via precipitation with ether. The solution of the resultant product is freeze-dried, gel-filtered, and purified by reverse phase HPLC to obtain the desired peptide. When utilizing the Boc system to perform the solid phase synthesis, preferably the resin is the PAM resin linked to the C-terminal amino acid of the peptide. The structure of the PAM resin is polystyrene, and the arm between the resin and the amino acid is 4-hydroxylmethyl phenylacetamide. In the Boc synthesis system, in the circle of deprotection, neutralization, and coupling, TFA/dichloromethane (DCM) is used to remove the protective group Boc, and diisopropylethylamine (DIEA)/dichloromethane is used for neutralization. After completion of peptide chain condensation, hydrogen fluoride (HF) containing p-methylphenol (5-10%) is used to treat the resin for 1 hour at 0° C., then the peptide chain is cleaved from the resin and the protective groups are removed at the same time. 50-80% acetic acid (containing a small amount of mercaptoethanol) is used to extract the peptide. The solution is freeze-dried, and then further isolated and purified by molecular screen Sephadex G10 or Tsk-40f. Then the desired peptide is obtained via high pressure liquid purification. Various coupling agents and coupling methods known in the peptide chemistry can be used to couple each amino acid residue. For example, dicyclohexylcarbodiimide (DCC), hydroxylbenzotriazole (HOBt) or 1,1,3,3-tetramethyluronium Hexafluorophosphate (HBTU) can be used for direct coupling. The purity and structure of the resultant short peptide can be verified by reverse phase HPLC and mass spectrometry.

In a preferred embodiment, the polypeptide of the present invention is prepared by solid phase method according to its sequence, purified by high performance liquid chromatography, thereby obtaining freeze-dried powder of target peptide with high purity. The powder is stored at $-20°$ C.

Another method is to produce the polypeptide of the present invention by a recombinant technique. With the conventional recombinant DNA technique, the polynucleotide of the present invention can be used to express or produce the recombinant polypeptide of the present invention. Generally, the method comprises the following steps:

(1) Transforming or transfecting a suitable host cell with a polynucleotide or variant thereof encoding the polypeptide of the present invention or a recombinant expression vector containing said polynucleotide;
(2) Culturing the host cell in a suitable culture medium;
(3) Isolating and purifying protein from the culture medium or cell.

The recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to, conventional renaturation treatment, treatment by protein precipitant (such as salt precipitation), centrifugation, cell lysis by osmosis, sonication, supercentrifugation, molecular sieve chromatography (gel chromatography), adsorption chromatography, ion exchange chromatography, high performance liquid chromatography (HPLC), and any other liquid chromatography, and the combination thereof.

It is also contemplated to link multiple polypeptides of the present invention in series due to their short length. After recombinant expression, the expression product can be obtained. Then the product is enzymatically cleaved to form the desired small peptides.

Cell Penetrating Element

As used herein, the term "cell-penetrating element(s)", "cell-penetrating peptide(s)" can be used interchangeably. Both of them refer to a small peptide fragment which helps to infiltrate the inhibitory peptide into cell effectively without affecting the activity of the inhibitory peptide and without causing damage to the cells. In a preferred embodiment, the sequences useful as the cell-penetrating elements in the present invention include, but are not limited to the following small peptides, such as RRMKWKK (SEQ ID NO.:13), GRKKRRQRRR (SEQ ID NO.: 14) or KKKRKV (SEQ ID NO. 15).

Liposome Preparation

A liposome as defined in pharmacy refers to microvesicles formed by encapsulating a medicine in lipid-like bilayer. Liposomes are formed by hydrophobic action of phospholipid molecules in the aqueous phase. So the preparation of liposome is not emphasized by membrane assembly, but how to form vesicles with an appropriate size, high entrapment efficiency and high stability. When using different method of preparation, the size of liposome may vary from tens of nanometers to several micrometers, and the structure is also different. The liposome preparation of the present invention refers to a preparation in which the polypeptide of the present invention or a modified polypeptide thereof is prepared into a liposome form by a conventional method. Preferred methods of preparation include membrane dispersion, surfactant dialysis, and ethanol injection. Preferably, the present invention provides an acyl modified liposomal formulation.

Pharmaceutical Composition and Methods of Administration

In another aspect, the present invention further provides a pharmaceutical composition, comprising (a) a safe and effective amount of the polypeptide of the present invention or a pharmaceutically acceptable salt thereof, and (b) a pharmaceutically acceptable carrier or excipient. The amount of the polypeptide of the present invention generally is 10 µg to 100 mg per dose, preferably 100-1000 µg per dose.

For the purpose of the invention, the effective dose is to administer an individual about 0.01 mg to 50 mg of the polypeptide of the present invention per kg body weight, preferably 0.05 mg to 10 mg of the polypeptide of the present invention per kg body weight. Further, the polypeptide of the present invention can be used alone, or in combination with the other therapeutic agents (for example, formulating into the same pharmaceutical composition).

The pharmaceutical composition can further comprise a pharmaceutically acceptable carrier. The term "pharmaceutically acceptable carrier" refers to the carrier for using in administering the therapeutic agents. The term refers to such medical carriers that they themselves do not induce antibody deleterious to the subject having been administered the composition, and they do not have excessive toxicity after administration. These carriers are well known by the skilled person in the art. And detailed discussion about the pharmaceutically acceptable excipient can be found in Remington's Pharmaceutical Sciences (Mack Pub. Co., N.J., 1991). Such carriers include, but are not limited to, saline, buffer solution, glucose, water, glycerin, ethanol, adjuvant or the combination thereof.

The pharmaceutically acceptable carrier in the therapeutic composition can comprise solution, such as water, saline, glycerin, and ethanol. Further, these carriers can contain auxiliary substance(s), such as wetting agent or emulsifying agent, pH buffering substance, etc.

Typically, the therapeutic composition can be formulated into an injectable formulation, such as a liquid solution or suspension; or it may be in a solid form that is suitable to be formulated into a solution or suspension or liquid carrier before injection.

Once formulating the composition of the present invention, it can be administered via conventional routes, including but are not limited to, administering intratumorally, intramuscularly, intravenously, via hepatic artery, orally, subcutaneously, intracutaneously or topically. The subject to be prevented or treated may be an animal, especially a human.

When the pharmaceutical composition of the present invention is used in the actual treatment, the dosage form of the pharmaceutical composition may vary according to the uses. Preferably, the dosage form is intravenous or arteria hepatica formulation, or injection for intratumorally administration.

The pharmaceutical composition can be formulated by mixing, diluting or dissolving according to the conventional methods. And, occasionally, suitable medical additives, such as excipients, disintegrating agents, adhesives, lubricants, diluting agents, buffering agents, isotonicities, preservatives, wetting agents, emulsifying agents, dispersing agents, stabilizing agents, and solubility promoters, may be added. Formulating can be carried out in a conventional manner according to the dosage form.

For example, an liquid formulation for intravenous administration can be done as follows: dissolving the polypeptide of the present invention or a pharmaceutically acceptable salt thereof and the basic substances in sterile water (surfactant is dissolved in said water), adjusting osmotic pressure and alkalinity acidity to the physiological level, optionally adding suitable medical additives, such as preservatives, stabilizing agents, buffering agents, isotonicities, anti-oxidants and tackifiers, and then allowing them completely dissolved.

The pharmaceutical composition of the present invention can further be administered in a form of slow release agent. For example, the polypeptide of the present invention or salt thereof can be incorporated into the pill or microcapsule with the slow release polymer as the carrier, and then the pill or microcapsule is implanted into the tissue to be treated by operation. Examples of the slow release polymer include ethylene-ethylene acetate copolymer, polyhydroxymethylacrylate, polyacrylamide, polyvinylpyrrolidone, methyl cellulose, polymer of lactic acid, lactic acid-glycolic acid copolymer, etc. Preferable examples of the slow release polymer include the biodegradable polymers, such as polymer of lactic acid, and lactic acid-glycolic acid copolymer.

When the pharmaceutical composition of the present invention is used in the actual treatment, the dose of the polypeptide of the present invention or a pharmaceutically acceptable salt thereof, as an active ingredient, can be suitably determined according to the body weight, age, sex, symptom of each patient.

Beneficial Effects of the Present Invention

1. The polypeptide of the present invention can competitively inhibit the formation of YAP-TEAD complexes, thus inhibiting growth of hepatoma cells and inducing death of hepatoma cells.

2. The polypeptide of the present invention can form an internal disulfide linkage, which stabilize the polypeptide structure and make half-life in the blood up to 24 hours or more.

3. The polypeptide of the present invention has a cell-penetrating element so that it can efficiently enter into the hepatoma cells and inhibit the activity of YAP. The invading rate of cancer cell reaches up to 80%, and the inhibitory polypeptide is prepared which has better (even superior) activity of inhibiting YAP protein.

4. The length and location of the disulfide linkage in the polypeptide of the present invention can be changed according to the core sequence, or few individual amino acids in the core sequence are replaced to some extent. The modified polypeptide still has the YAP inhibitory activity, and has better stability.

5. The acylated polypeptide of the present invention can be prepared more efficiently as a liposome preparation with an improved membrane penetrating property, resulting in more efficient inhibitory activity on tumors.

The present invention will be further illustrated below with reference to the specific examples. It should be understood that these examples are only to illustrate the invention but not to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Unless indicated otherwise, parts and percentage are weight parts and weight percentage.

General Methods

TR-FRET Test

As a screening method of YAP inhibiting polypeptide, the test is based on the time-resolved fluorescence energy transfer via the micro-plate reader. The YAP inhibiting polypeptide and its target TEAD are labeled with two fluorophores. The interaction of the two molecules makes the two fluorophores close to each other and generate energy transfer, and then fluoresce at specific wavelength is transmitted. Potential YAP inhibiting peptides is selected in a short time by measuring the specific wavelength via the micro-plate reader. The principle of the test is shown in FIG. 1.

| | Peptide Sequence |
|---|---|
| SEQ ID NO.: | Sequence |
| 1 | VPMRLRKLPDSFFKPPE |
| 2 | VPM(Hcy)LRKLPDSFCKPPE |
| 3 | VPM(Hcy)LRKLPDSFCKPPRRMKWKK |
| 4 | VPF(Hcy)LRKLPDSFCKPPE |
| 5 | VPF(Hcy)LR(Orn)LPDSFCKPPE |
| 6 | VPF(Hcy)LR(Dab)LPDSFCKPPE |
| 7 | VPF(Hcy)LR(Dab)LPDSFCKPPRRMKWKK |
| 8 | VPMCLRKLPESFCHPPE |
| 9 | VPM(Hcy)LRKLPCSFCDPPE |
| 10 | PQTVPMRLRKLPDSFFKPPE |
| 11 | VPM(Hcy)LRK(Nle)PASFCKPPE |
| 12 | VP(3-Cl)F(Hcy)LRK(Nle)PASFCKPPE |
| 13 | RRMKWKK |
| 14 | RGRKKRRQRRR |
| 15 | KKKRKV |

Example 1

Screening of YAP Inhibitory Polypeptides 1.1 The inventor constructed different phage peptide libraries based on the arrangement of YAP protein. Candidate polypeptides inhibiting the binding of YAP-TEAD were selected after many screening tests. Then the inhibitory polypeptides which could efficiently penetrate cells, decrease activity of TEAD and down-regulate other YAP target genes were selected from the numerous candidate peptides. The screened YAP inhibiting polypeptides were confirmed via test-tube and PTDX animal model study. The YAP inhibiting polypeptides with successful therapeutic effect were finally obtained.

The results showed that YAP (AA50-171) embraced the orbicular structure of TEAD1 (AA194-411), and formed a broad interaction via three highly conserved protein interfaces. Interface 1 was the antiparallel β lamellar structure of YAPβ1 (AA53-58) and TEADβ7. Interface 2 was the mutual structure between YAP1α1 (AA61-73) helix and TEAD α3 and TEAD α4 helix. The interface 3 was a deep pocket region (FIG. 1) formed by the binding between YAP (AA86-100) helical region and TEAD1 β4, β11, β12, α1, and α4.

1.2 The cell-penetrating element (SEQ ID NO.: 13) in Example 2 was linked to the N-terminal of the candidate sequences (SEQ ID NOs.:1, and 16-20) based on the preliminary screened inhibitory sequence of YAP protein. The sequences of Some of the candidate polypeptides are shown in following table:

TABLE 6

| SEQ ID NO.: | Location of YAP | Sequence |
|---|---|---|
| 16 | aa24-40 | PQGQGPPSGPGQPAPA |
| 17 | aa54-70 | IVHVRGDSETDLEALF |
| 1 | aa84-100 | VPMRLRKLPDSFFKPPE |
| 18 | aa114-130 | TAGALTPQHVRAHSSP |
| 19 | aa144-160 | PTGVVSGPAATPTAQH |
| 20 | aa174-190 | PAGWEMAKTSSGQRYF |

By using the polypeptide sequences in Table 6, the dose-effect relationship between cell proliferation inhibition and polypeptide dosage of tumor cell lines exhibiting different levels of YAP expression was determined.

The hepatoma cell line BEL7404 (purchased from The Chinese Academy of Sciences cell bank) was a cell line with high expression of YAP protein; HCCLM3 (purchased from The Chinese Academy of Sciences cell bank) was a cell line with low expression of YAP protein. The hepatoma cell lines (BEL7404 or HCCLM3) were inoculated into a 96-well plate at the concentration of 2000 cells/well, and incubated overnight in RPMI1640 containing 1% bovine serum at 37° C. The hepatoma cell lines were treated with polypeptides having different concentrations at 37° C. for 72 h.

Figure 4:
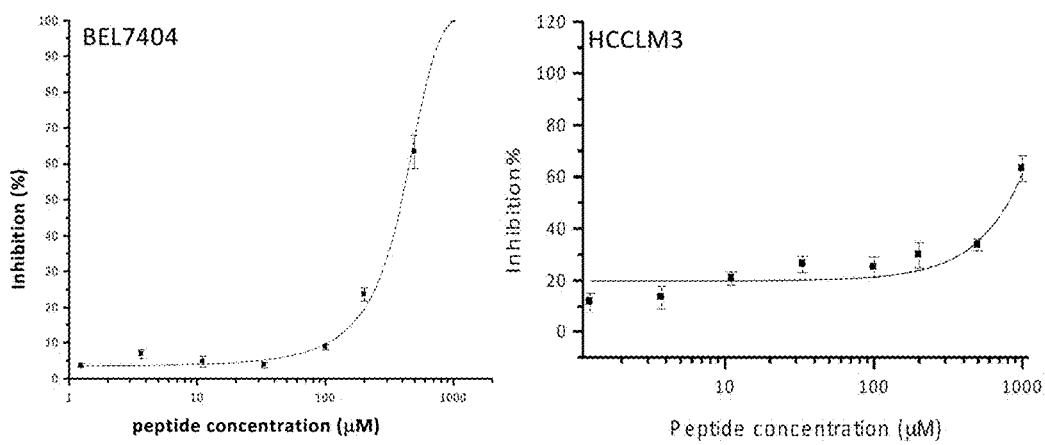
FIG. 4 shows a dose-effect relationship between the polypeptide of SEQ ID NO.: 1 and cell proliferation in tumor cell lines with high YAP protein expression or low YAP protein expression, respectively.

The results showed that the polypeptide represented by SEQ ID NO.: 1 showed a more significant anti-proliferative effects on cancer cells in a certain concentration than other peptides, no matter the cell was a YAP protein high expression cell line or low expression cell line (FIG. 4). The inhibition on cell lines BEL7404 with high expression of YAP protein was more significant. It can be seen that, the polypeptides of the present invention exhibited excellent inhibition on cell lines with high expression of YAP protein.

Moreover, $IC_{50}$ values of the cells in 1.1 were determined using CCK-8 kit.

The results were shown in Table 7. The polypeptides represented by SEQ ID NO.: 16, and 17 exhibited very low $IC_{50}$ values in the cell lines with high expression of YAP protein, but exhibited little effect on the cell lines with low expression of YAP protein. As to the polypeptide of SEQ ID NO.: 1, which exhibited lower $IC_{50}$ values in the cell lines with high expression of YAP protein, it also exhibited the lowest $IC_{50}$ value in the cell lines with low expression of YAP protein. After comprehensive consideration, the polypeptide represented by SEQ ID NO.: 1 could be regarded as the polypeptide exhibiting the strongest inhibitory activity, which could inhibit the binding between YAP and TEAD.

TABLE 7

| | IC$_{50}$ values of the polypeptides at a concentration of 1% in 72 h (μM) | | | | | |
|---|---|---|---|---|---|---|
| | SEQ ID NO.: 16 | SEQ ID NO.: 17 | SEQ ID NO.: 1 | SEQ ID NO.: 18 | SEQ ID NO.: 19 | SEQ ID NO.: 20 |
| BEL7404 | 241.5 ± 27.2 | 210.9 ± 44.2 | 387.9 ± 43.6 | 816.3 ± 14.4 | 762.9 ± 31.5 | 444.1 ± 46.5 |
| HCCLM3 | >1000 | >1000 | 808.6 ± 27.4 | >1000 | >1000 | >1000 |

Example 2

Modification of YAP Inhibitory Polypeptides

It was discovered that the polypeptide represented by SEQ ID NO.: 1 was difficult for effective uptake by cells and exhibited low stability, although the polypeptide could combine with TEAD in vitro.

In this example, the sequence was modified based on SEQ ID NO.: 1. Some preferred modification based on the tested results included: adding a disulfide linkage within the peptide, or adding a cell-penetrating element.

The test results were shown in table 2.

TABLE 2

| Peptide | Structure | Percentage of Cell penetration or infiltration (%) | Stability * (4 h) | Stability * (>24 h) |
|---|---|---|---|---|
| Peptide 1 | | <10 | 0 | 0 |
| Peptide 2 | Peptide + Disulfide linkage | 8 | 93 | 13 |
| Peptide 3 | Peptide + Cell-penetrating element 1 (RRMKWKK, SEQ ID NO.: 13) | 100 | 49 | 3 |
| Peptide 4 | Peptide + Cell-penetrating element 2 (RGRKKRRQRRR, SEQ ID NO.: 14) | 135 | ND | ND |

* The stability referred to the tested stability in plasma, and it was the percentage of residual peptides after a period of the testing time.

The results showed that the polypeptide represented by SEQ ID NO.: 1 exhibited a significantly improved stability in plasma when a disulfide linkage was introduced. In addition, when the cell-penetrating element (RRMKWKK or RGRKKRRQRRR)(SEQ ID NO.: 34) were added at the terminal of polypeptides, the percentage of polypeptides that penetrated into was increased from less than 10% to 100% (taking percentage of penetration for the peptide with RRMKWKK as 100%) or 135%.

Example 3

Modification of the YAP Inhibitory Polypeptides

Modification based on polypeptide SEQ ID NO.: 1:
(a). The disulfide linkage was introduced in the peptide of SEQ ID NO.: 1, and the modified sequence was represented in SEQ ID NO.: 2.
(b). $X_4$ was replaced by Orn or Dab respectively based on the sequence of SEQ ID NO.: 2, and the modified sequence was represented by SEQ ID NOs.: 5 or 6.

For the YAP inhibitory polypeptides modified in above (a) and (b), the IC$_{50}$ values for TEAD binding and the stability in plasma were measured. The test results were shown in table 3.

TABLE 3

| SEQ ID NO.: | IC$_{50}$ | Stability* (4 h) | Stability* (>24 h) |
|---|---|---|---|
| 2 | 23 nM | 92% | 7% |
| 5 | 43 nM | 99% | 51% |
| 6 | 28 nM | 98% | 53% |

The results showed that the plasma stability of the polypeptides after introducing a disulfide linkage was improved significantly and the stability were even more excellent with further modification of the polypeptides. Moreover, the IC$_{50}$ values of all modified polypeptides were in nano molar order.

Example 4

Modification of the YAP Inhibitory Polypeptides

The peptide SEQ ID NO.:2 in example 3 was further modified, and the difference was that $X_5$ and $X_7$ were replaced by E and H, or by C and D, respectively, and a disulfide linkage was formed between $X_2$ and $X_6$. The sequences of the modified peptides were represented by SEQ ID NOs.: 8 and 9. The IC$_{50}$ values for TEAD binding and stability in plasma were measured. The results were shown in table 4.

TABLE 4

| SEQ ID NO.: | IC$_{50}$ | Stability* (4 h) | Stability* (>24 h) |
|---|---|---|---|
| 8 | 28 nM | 105% | 62% |
| 9 | 25 nM | 100% | 55% |

The results showed that the plasma stability of the further modified polypeptides was improved significantly, and the IC$_{50}$ values of all modified polypeptides were in nano molar order.

Example 5

Modification of the YAP Inhibitory Polypeptides

The peptide SEQ ID NO.:1 of the present invention was modified. The modified polypeptides were tested to measure IC$_{50}$ values for TEAD binding and stability in plasma. The results were shown in table 5.

TABLE 5

| SEQ ID NO.: | Sequences | IC$_{50}$ |
|---|---|---|
| 1 | VPMRL RKLPD SFFKP PE | 49 μM |
| 10 | PQT VPMRL RKLPD SFFKP PE | 37 μM |

TABLE 5-continued

| SEQ ID NO.: | Sequences | $IC_{50}$ |
|---|---|---|
| 11 | VPM(Hcy)L RK(Nle)PA SFCKP PE | 15 nM |
| 12 | VP(3-Cl)F(Hcy) L RK(Nle)PA SFCKP PE | 23 nM |

Example 7

Modification and Activity Tests of the YAP Inhibitory Polypeptides

The polypeptide represented by SEQ ID NO.:1 was further modified. The $IC_{50}$ values of the polypeptides at a concentration of 1% in cell cultivating for 72 h were measured. The peptide sequences and test results were shown in table 8.

TABLE 8

| SEQ ID NO.: | Sequences | Location of disulfide linkage | $IC_{50}$ BEL7404 | $IC_{50}$ HCCLM3 |
|---|---|---|---|---|
| 21 | VP(3-Cl)F-Hcy-LRK-Nle-PASFCKPP RRMKWKK | {Hcy4, Cys13} | 28.6 ± 2.9 | 196.4 ± 16.3 |
| 22 | VP(3-Cl)F-Hcy-LRK-Nle-PESFCKPP RRMKWKK | {Hcy4, Cys13} | 67.9 ± 6.4 | 180.9 ± 21.7 |
| 23 | VP(3-Cl)F-Hcy-LKK-Nle-PASFCKPP RRMKWKK | {Hcy4, Cys13} | 37.2 ± 1.0 | 128.9 ± 26.4 |
| 24 | VP(3-Cl)F-Hcy-LKR-Nle-PASFCKPP RRMKWKK | {Hcy4, Cys13} | 25.7 ± 3.0 | 67.3 ± 38.5 |
| 25 | AP(3-Cl)F-Hcy-LKK-Nle-PDSFCKPP RRMKWKK | {Hcy4, Cys13} | 119.1 ± 7.1 | >1000 |
| 26 | AP(3-Cl)F-Hcy-Nle-KK-Nle-PDSFCKPP RRMKWKK | {Hcy4, Cys13} | 62.7 ± 5.9 | >1000 |
| 27 | VP(3-Cl)F-Hcy-LKK-Nle-PDSFCKPP RRMKWKK | {Hcy4, Cys13} | 60.2 ± 15.2 | >1000 |
| 28 | VP(3-Cl)F-Hcy-Nle-KK-Nle-PDSFCKPP RRMKWKK | {Hcy4, Cys13} | 55.4 ± 6.3 | 198.3 ± 19.6 |
| 29 | VP(3-Cl)F-Hcy-LKK-Nle-PESFCKPP RRMKWKK | {Hcy4, Cys13} | 65.6 ± 8.9 | 254 ± 12.3 |
| 30 | VP(3-Cl)F-C-LKK-Nle-PASF-Hcy-KPP RRMKWKK | {Cys4, Hcy13} | 28.2 ± 1.8 | 142.5 ± 9.4 |
| 31 | VP-Hcy-(3-Cl)F-LKK-Nle-PASCFKPP RRMKWKK | {Hcy3, Cys12} | 16.2 ± 1.9 | 106.9 ± 23.2 |
| 32 | VP(3-Cl)F-L-Hcy-KK-Nle-PASFKCPP RRMKWKK | {Hcy5, Cys14} | 38.4 ± 3.8 | 318.9 ± 17.5 |
| 33 | VP(3-Cl)F-LKK-Hcy-Nle-PASFKPPC RRMKWKK | {Hcy7, Cys16} | 10.8 ± 2.1 | 81.1 ± 13.1 |

Note:
(3-Cl)F means 3-phenylalanine.

The results showed that the polypeptides of the present invention could inhibit the binding between YAP and TEAD more efficiently.

Example 6

Screening Test of Activity Via Alanine Scanning

In this example, each amino acid in the sequence of SEQ ID NO.: 1 was screened via alanine scanning and replacing. The results showed that the polypeptides replaced by different amino acids showed 30%-120% activity of the polypeptide of SEQ ID NO.: 1. However, when the amino acids of 7 sites (M86, R89, L91, P92, S94, F95, F96) corresponding to positions 86-96 in YAP were replaced by Ala, the activity of replaced peptides was relatively lower. Therefore, these sites could be regarded as key amino acid sites in the polypeptides of the present invention (located in aa 86-96 and corresponding to positions Z3-Z13 in Formula Va). It suggested that these sites should be retained or be conservatively substituted in the further experiments.

The results showed that all of the modified sequences shown good YAP inhibitory activity; wherein the polypeptides represented by SEQ ID NOs.: 21, 23, 31, or 33 shown best inhibitory activity. In addition, it was found that, when the amino acids of key sites in Example 7 were conservatively substituted or a disulfide linkage was formed by replacement, for example when the amino acids corresponding to sites Z4 and Z13 were removed and amino acids for forming a disulfide linkage were added, the obtained polypeptides could still maintain good YAP inhibitory activity.

Example 8

Animal Experiments

YAP expression for tumor samples of the tumor xenograft models from 40 different liver cancer patients was analyzed. Two tumor xenograft models from liver cancer patients with high YAP expression were selected and inoculated in mouse subcutis to form a tumor. Once the subcutaneous tumor volume was larger than 0.2 cm$^3$, tumor mice were randomly assigned into untreated group or to test group receiving 75 mg/kg YAP inhibiting peptides (SEQ ID NOs.:21, 23, 31 and 33) by intra-tumor injection for three weeks, and three times a week. The tumor volume was measured with a vernier caliper three times a week.

Figure 5:
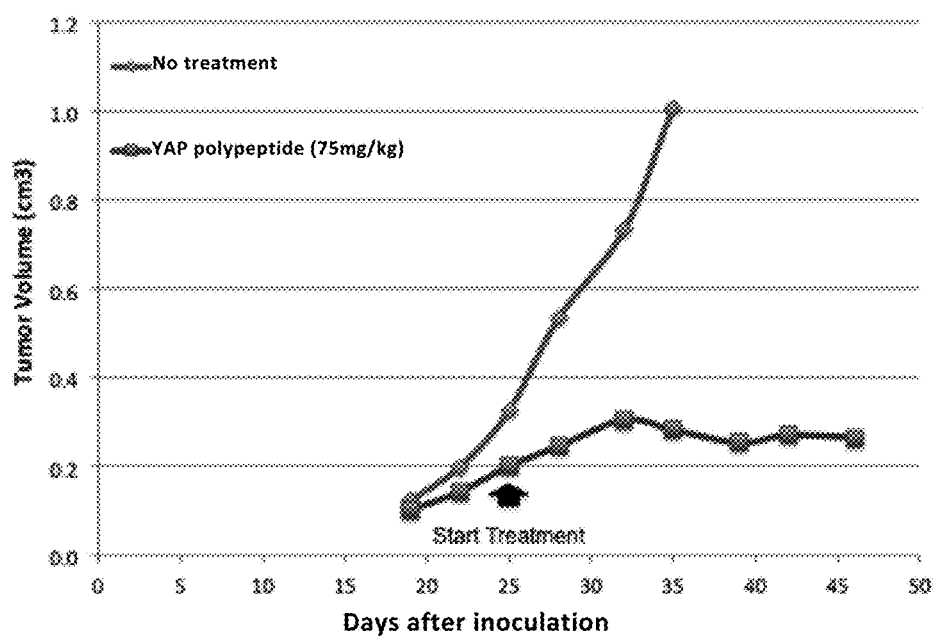
FIG. 5 shows that after administrating YAP inhibiting polypeptide of the present invention, the volume of tumor was significantly smaller than that of blank control in an in vivo experiment.

The results showed that all of the above YAP inhibiting polypeptides could significantly inhibit the tumor growth. The inhibitory rate (tumor size of the test group/tumor size of the control group) was far above 50% (P<0.05) after about one week treatment (or 30th days since the experiment commenced). The inhibitory curve of SEQ ID NO.:23 was shown in FIG. 5.

Example 9

Preparation of Modified Peptide

The transmembrane fragment of the sequence shown in SEQ ID NO.: 33 was replaced with "GRKKRRQRRR" and subjected to a series of modification.

Specifically, the peptide sequences as shown in Table 9 were synthesized from the C-terminus to the N-terminus direction using a manual solid-phase Fmoc method using the Rink Amide MBHA resin as the starting material.

TABLE 9

| SEQ ID NO: | Sequence | Modification | Name of modified polypeptide | Position of disulfide bond |
|---|---|---|---|---|
| 35 | VP (3-Cl) F-LKK-Hcy-Nle-PASFKPPC GRKKRRQRRRK K | Stearylation of K at C terminal | P47 | {Hcy7, Cys16} |
| 36 | VP (3-Cl) F-LKK-Hcy-Nle-PASFKPPC GRKKRRQRRR K | Stearylation of K at C terminal | P48 | {Hcy7, Cys16} |
| 37 | VP (3-Cl) F-LKK-Hcy-Nle-PASFKPPC K | Stearylation of K at C terminal | P49 | {Hcy7, Cys16} |

The resin was grafted with 3 equivalents of Fmoc-Lys (Dde)—OH/HOBt/DIC so as to introduce the second amino acid residue at the C-terminus. Then, 25% hexahydropyridine/DMF (volume ratio) was used to remove the N-terminal Fmoc protecting group so that the N-terminus became a free amino group. The amino acid residues were then ligated in turn to complete synthesis of the entire polypeptide. After N-terminal was capped with acetylation (3 equivalents of $Ac_2O$, 6 equivalents of diisopropylethylamine), the Dde protecting group at side chain of C-terminal Lys was removed with 2% hydrazine hydrate/DMF solution. After direct reaction of stearoyl chloride (C18 acyl halide) with the side chain amino groups of the C-terminal Lys of the polypeptide of the invention, the modified stearoylated polypeptides P47, P48 and P49 as shown in SEQ ID NO.: 35-37 were obtained.

Example 10

Preparation of Liposome Formulations

The stearylated polypeptides P47, P48 and P49 were prepared into liposome formulations by using different methods. The methods were as follows:

10.1 Preparation of P49 Liposome, Code Number 1.1
Methods: Thin Film Dispersion Method The peptide and liposome (HSPC+CHOL) were mixed well in a molar ratio of 1:20 ratio in the eggplant-shaped bottle. After the mixture was dried with nitrogen, 5% glucose was added and ultrasonic hydration was conducted. The mixture was filtrated and a lipid suspension was obtained and dialysis was conducted.

10.2 Preparation of P49 Liposome, Code Named 1.2
Methods: Surfactant Dialysis

The liposome (HSPC+CHOL) and chloroform were mixed in eggplant vials. After the mixture was dried with nitrogen, 5% glucose was added and ultrasonic hydration was conducted. The mixture was filtrated to obtain lipid suspension. The polypeptide was mixed with 5% glucose and octylglucoside (OG), injected into the lipid suspension at a molar ratio of 1:3, shaken and dialyzed.

10.3 Preparation of P48 Liposome, Code Named 2.1
Method: Ethanol Injection Method The liposome (HSPC+CHOL) and chloroform were mixed in eggplant vials. After the mixture was dried with nitrogen, 5% glucose was added and ultrasonic hydration was conducted. The mixture was filtrated to obtain lipid suspension. The polypeptide and ethanol were prepared into solution, and injected into the lipid suspension at a molar ratio of 1:10, filtrated and dialyzed.

10.4 Preparation of P48 Liposome, Code Named 2.2
Method: Ethanol Injection Method The liposome (HSPC+CHOL) and chloroform were mixed in eggplant vials. After the mixture was dried with nitrogen, 5% glucose was added and ultrasonic hydration was conducted. The mixture was filtrated to obtain lipid suspension. The polypeptide and ethanol were prepared into solution, and injected into the lipid suspension at a molar ratio of 1:20, filtrated and dialyzed.

10.5 Preparation of P48 Liposome, Code Named 1.3
Methods: Surfactant Dialysis

The liposome (HSPC+CHOL) and chloroform were mixed in eggplant vials. After the mixture was dried with nitrogen, 5% glucose was added and ultrasonic hydration was conducted. The mixture was filtrated to obtain lipid suspension. The polypeptide was mixed with 5% glucose and OG, injected into the lipid suspension at a molar ratio of 1:3, shaken and dialyzed.

10.6 Preparation of P47 Liposome, Code Named 3.1
Methods: Surfactant Dialysis

The liposome (HSPC+CHOL) and chloroform were mixed in eggplant vials. After the mixture was dried with nitrogen, 5% glucose was added and ultrasonic hydration was conducted. The mixture was filtrated to obtain lipid suspension. The polypeptide was mixed with 5% glucose and OG, injected into the lipid suspension at a molar ratio of 1:5, shaken and dialyzed.

10.7 Preparation of P47 Liposome, Code Named 3.2
Methods: Surfactant Dialysis

The liposome (HSPC+CHOL) and chloroform were mixed in eggplant vials. After the mixture was dried with nitrogen, 5% glucose was added and ultrasonic hydration was conducted. The mixture was filtrated to obtain lipisuspension. The polypeptide was mixed with 5% glucose and OG, injected into the lipid suspension at a molar ratio of 1:3, shaken and dialyzed. d

Example 11

Characterization of Liposome Formulation of Polypeptide

P47, P48, and P49 Liposome Preparations Prepared in Example 10 were Characterized by Conventional Methods:

TABLE 10

| Sample Name | Batch code | Liposome Preparation Method | Polypeptide/ Liposome ratio | Particle size (nm) | PDI | Zeta Potential (mv) | Encapsulation rate |
|---|---|---|---|---|---|---|---|
| P49 liposome | 1.1 | film dispersion | 1:20 | 114.2 | 0.151 | 40.7 | 15.89% |
| | 1.2 | Surfactant dialysis | 1:3 | 86.51 | 0.222 | 35 | 45.86% |
| | 1.1 | film dispersion | 1:20 | 148.6 | 0.09 | 36.6 | 7.94% |
| | 1.2 | Surfactant dialysis | 1:3 | 126.9 | 0.109 | 42.5 | 38.22% |
| | 1.2 | Surfactant dialysis | 1:3 | 223.4 | 0.177 | 53.9 | 47.21% |
| P48 liposome | 2.1 | ethanol injection (ethanol:water = 1:9) | 1:10 | 156.5 | 0.064 | 44.1 | 35.34% |
| | 2.2 | ethanol injection (ethanol:water = 1:9) | 1:20 | 102.2 | 0.11 | 41.4 | 42.74% |
| | 2.3 | Surfactant dialysis | 1:3 | 133.4 | 0.083 | 44.3 | 39.11% |
| | 2.1 | ethanol injection (ethanol:water = 1:9) | 1:10 | 90.5 | 0.131 | 47.7 | 23.48% |
| | 2.2 | ethanol injection (ethanol:water = 1:9) | 1:20 | 129.9 | 0.061 | 38.1 | 19.78% |
| | 2.3 | Surfactant dialysis | 1:3 | 167.5 | 0.076 | 37.2 | 51.92% |
| | 2.3 | Surfactant dialysis | 1:3 | 108.8 | 0.247 | 62.2 | 38.81% |
| P47 liposome | 3.1 | Surfactant dialysis | 1:5 | 138.3 | 0.039 | 32.6 | 56.20% |
| | 3.2 | Surfactant dialysis | 1:3 | 100.1 | 0.117 | 34 | 55.72% |
| | 3.1 | Surfactant dialysis | 1:5 | 139.2 | 0.049 | 29.2 | 59.06% |
| | 3.2 | Surfactant dialysis | 1:3 | 144.6 | 0.049 | 32.2 | 61.86% |
| Only liposome | / | film dispersion | / | 164 | 0.078 | 6.82 | / |
| | / | Surfactant dialysis | / | 1458 | 0.414 | / | / |

As can be seen from Table 10, various conventional methods for preparing liposome can be used to prepare the modified polypeptides of the present invention into liposome formulations wherein the surface activity dialysis has the highest encapsulation efficiency and is preferably used in the following experiments for preparation of liposome formulation.

Example 12

Cell Proliferation Inhibition Experiment of Polypeptide Liposome Formulation The liposome formulations prepared in Example 10 were subjected to cell experiments. The steps were as follows:

BEL7404 (ATCC) cells were seeded in 96-well plates at a density of 2000 cells/well and 1640 medium containing 1% FBS. MHCC97L (ATCC) cells were seeded in 96-well plates with 10% FBS DMEM medium at a density of 4000 cells/well and incubated overnight at 37° C. The cells were treated with the polypeptide liposome formulations prepared in Example 10 (9 concentrations, 50 uM was used as the initial concentration and it was half-diluted to obtain 9 concentrations. The IC50 values were calculated). Then, BEM7404 and MHCC97L cells were treated with 1640 medium containing 1% FBS or DMEM medium containing 10% FBS and incubated at 37° C. for 72 hours. The cell viability was determined by CCK-8 kit. The results showed that the IC50 value of the polypeptide liposome formulation was very low, indicating a significant inhibitory effect on tumor cells. The results were shown in Table 11.

TABLE 11

| | Cell proliferation test results | |
|---|---|---|
| | BEL7404 | MHCC97L |
| Sample name | $IC_{50}$ (uM) | $IC_{50}$ (uM) |
| P49 liposome | 0.47 ± 0.04 | 8.18 ± 0.35 |
| P48 liposome | 0.69 ± 0.09 | 3.71 ± 0.42 |
| P47 liposome | 1.21 ± 0.81 | / |
| Blank liposome | >1000 | >1000 |

"/" means that the test was not conducted.

Comparative Example 1

Cell Inhibition Experiments Using Unmodified YAP Inhibitory Polypeptide

In this example, an unmodified YAP inhibitory polypeptides (an original polypeptide without acylation or without any membrane penetrating fragment, or a acylated modified peptide without being encapsulated by liposome) were used to test and compare the inhibitory effect on cells.

TABLE 12

| polypeptide/ modified polypeptide/ liposome formulation | acylation | Liposomeen capsulation | BEL7404 IC50 (uM) | MHCC97L IC50 (uM) |
|---|---|---|---|---|
| P44 polypeptide (SEQ ID NO.: 38, VP (3-Cl) F-LKK-Hcy-Nle-PASFKPPC) | non-acylation | liposome | / | / |
| P48 polypeptide (SEQ ID NO.: 36) | acylation ($C_{20}$) | liposome | 3.36 ± 0.58 | 5.39 ± 1.85 |
| P48 polypeptide (SEQ ID NO.: 36) | acylation ($C_{20}$) | Non-liposome | 4.05 ± 1.60 | 6.53 ± 0.58 |
| P49 polypeptide (SEQ ID NO.: 37) | acylation ($C_{12}$) | liposome | 1.56 ± 0.42 | 8.4 ± 0.56 |
| P49 polypeptide (SEQ ID NO.: 37) | acylation ($C_{12}$) | Non-liposome | 2.02 ± 0.39 | 7.83 ± 2.69 |

As can be seen from Table 11, in the non-acylated polypeptides, some had defects such as failure to form liposome or low inhibitory efffect on cells. However, after the polypeptide of invention were was subjected to C10-C24 acylation modification, even if it was not prepared into a liposome formulation, the inhibitory efficiency on cells was greatly improved, and the IC50 value thereof was comparable to liposome formulation. It can be seen that the acylation of the polypeptide of invention can not only improve the formation of medicine, but also obtain a better inhibitory effect on cell proliferation.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

The invention claimed is:

1. An isolated polypeptide having the sequence as shown in SEQ ID NO: 37.

2. A modified polypeptide which is formed by acylation of a polypeptide having the sequence of SEQ ID NO: 37.

3. The modified polypeptide of claim 2, which has a structure as shown in formula B:

$$P_0\text{-}X_G \quad \text{formula B}$$

wherein $X_G$ represents $C_{10}$-$C_{24}$ acyl, and $P_0$ represents the sequence of SEQ ID NO: 37.

4. A pharmaceutical composition comprising a polypeptide having the sequence of SEQ ID NO: 37 or an acylated polypeptide of a polypeptide having the sequence of SEQ ID NO: 37 or a pharmaceutically acceptable salt of the polypeptide or the acylated polypeptide as an active ingredient.

* * * * *

SEQUENCE LISTING

```
<160> NUMBER OF SEQ ID NOS: 37

<210> SEQ ID NO 1
<211> LENGTH: 17
<212> TYPE: PRT
<213> ORGANISM: Homo sapiens

<400> SEQUENCE: 1

Val Pro Met Arg Leu Arg Lys Leu Pro Asp Ser Phe Phe Lys Pro Pro
1               5                   10                  15

Glu

<210> SEQ ID NO 2
<211> LENGTH: 17
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (4)..(4)
<223> OTHER INFORMATION: Xaa=Hcy

<400> SEQUENCE: 2

Val Pro Met Xaa Leu Arg Lys Leu Pro Asp Ser Phe Cys Lys Pro Pro
1               5                   10                  15

Glu

<210> SEQ ID NO 3
<211> LENGTH: 23
<212> TYPE: PRT
<213> ORGANISM: Artificial sequence
<220> FEATURE:
```

```
<223> OTHER INFORMATION: polypeptide
<220> FEATURE:
<221> NAME/KEY: misc_feature
<222> LOCATION: (4)..(4)
<223> OTHER INFORMATION: Xaa=Hcy

<400> SEQUENCE: 3

Val Pro Met Xaa Leu Arg Lys Leu Pro Asp Ser Phe Cys Lys Pro Pro
1               5                   10                  15

Arg Arg Met Lys Trp Lys Lys
            20

<210> SEQ ID NO 4
<211> LENGTH: 17
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (4)..(4)
<223> OTHER INFORMATION: Xaa=Hcy

<400> SEQUENCE: 4

Val Pro Phe Xaa Leu Arg Lys Leu Pro Asp Ser Phe Cys Lys Pro Pro
1               5                   10                  15

Glu

<210> SEQ ID NO 5
<211> LENGTH: 17
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (7)..(7)
<223> OTHER INFORMATION: Xaa=Orn

<400> SEQUENCE: 5

Val Pro Phe Xaa Leu Arg Xaa Leu Pro Asp Ser Phe Cys Lys Pro Pro
1               5                   10                  15

Glu

<210> SEQ ID NO 6
<211> LENGTH: 17
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (7)..(7)
<223> OTHER INFORMATION: Xaa=Dab

<400> SEQUENCE: 6

Val Pro Phe Xaa Leu Arg Xaa Leu Pro Asp Ser Phe Cys Lys Pro Pro
1               5                   10                  15

Glu
```

<210> SEQ ID NO 7
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (7)..(7)
<223> OTHER INFORMATION: Xaa=Dab

<400> SEQUENCE: 7

Val Pro Phe Xaa Leu Arg Xaa Leu Pro Asp Ser Phe Cys Lys Pro Pro
1               5                   10                  15

Arg Arg Met Lys Trp Lys Lys
            20

<210> SEQ ID NO 8
<211> LENGTH: 17
<212> TYPE: PRT
<213> ORGANISM: Artificial sequence
<220> FEATURE:
<223> OTHER INFORMATION: polypeptide

<400> SEQUENCE: 8

Val Pro Met Cys Leu Arg Lys Leu Pro Glu Ser Phe Cys His Pro Pro
1               5                   10                  15

Glu

<210> SEQ ID NO 9
<211> LENGTH: 17
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (4)..(4)
<223> OTHER INFORMATION: Xaa=Hcy

<400> SEQUENCE: 9

Val Pro Met Xaa Leu Arg Lys Leu Pro Cys Ser Phe Cys Asp Pro Pro
1               5                   10                  15

Glu

<210> SEQ ID NO 10
<211> LENGTH: 20
<212> TYPE: PRT
<213> ORGANISM: Artificial sequence
<220> FEATURE:
<223> OTHER INFORMATION: polypeptide

<400> SEQUENCE: 10

Pro Gln Thr Val Pro Met Arg Leu Arg Lys Leu Pro Asp Ser Phe Phe
1               5                   10                  15

Lys Pro Pro Glu
            20

<210> SEQ ID NO 11
<211> LENGTH: 17
<212> TYPE: PRT
<213> ORGANISM: Artificial sequence

```
<220> FEATURE:
<223> OTHER INFORMATION: polypeptide
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 11

Val Pro Met Xaa Leu Arg Lys Xaa Pro Ala Ser Phe Cys Lys Pro Pro
1               5                   10                  15

Glu

<210> SEQ ID NO 12
<211> LENGTH: 17
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 12

Val Pro Xaa Xaa Leu Arg Lys Xaa Pro Ala Ser Phe Cys Lys Pro Pro
1               5                   10                  15

Glu

<210> SEQ ID NO 13
<211> LENGTH: 7
<212> TYPE: PRT
<213> ORGANISM: Artificial sequence
<220> FEATURE:
<223> OTHER INFORMATION: cell penetrating element

<400> SEQUENCE: 13

Arg Arg Met Lys Trp Lys Lys
1               5

<210> SEQ ID NO 14
<211> LENGTH: 11
<212> TYPE: PRT
<213> ORGANISM: Artificial sequence
<220> FEATURE:
<223> OTHER INFORMATION: cell penetrating element

<400> SEQUENCE: 14

Arg Gly Arg Lys Lys Arg Arg Gln Arg Arg Arg
1               5                   10

<210> SEQ ID NO 15
<211> LENGTH: 6
<212> TYPE: PRT
<213> ORGANISM: Artificial sequence
<220> FEATURE:
<223> OTHER INFORMATION: cell penetrating element
```

```
<400> SEQUENCE: 15

Lys Lys Lys Arg Lys Val
1               5

<210> SEQ ID NO 16
<211> LENGTH: 16
<212> TYPE: PRT
<213> ORGANISM: Homo sapiens

<400> SEQUENCE: 16

Pro Gln Gly Gln Gly Pro Pro Ser Gly Pro Gly Gln Pro Ala Pro Ala
1               5                   10                  15

<210> SEQ ID NO 17
<211> LENGTH: 16
<212> TYPE: PRT
<213> ORGANISM: Homo sapiens

<400> SEQUENCE: 17

Ile Val His Val Arg Gly Asp Ser Glu Thr Asp Leu Glu Ala Leu Phe
1               5                   10                  15

<210> SEQ ID NO 18
<211> LENGTH: 16
<212> TYPE: PRT
<213> ORGANISM: Homo sapiens

<400> SEQUENCE: 18

Thr Ala Gly Ala Leu Thr Pro Gln His Val Arg Ala His Ser Ser Pro
1               5                   10                  15

<210> SEQ ID NO 19
<211> LENGTH: 16
<212> TYPE: PRT
<213> ORGANISM: Homo sapiens

<400> SEQUENCE: 19

Pro Thr Gly Val Val Ser Gly Pro Ala Ala Thr Pro Thr Ala Gln His
1               5                   10                  15

<210> SEQ ID NO 20
<211> LENGTH: 16
<212> TYPE: PRT
<213> ORGANISM: Homo sapiens

<400> SEQUENCE: 20

Pro Ala Gly Trp Glu Met Ala Lys Thr Ser Ser Gly Gln Arg Tyr Phe
1               5                   10                  15

<210> SEQ ID NO 21
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle
```

<400> SEQUENCE: 21

Val Pro Xaa Xaa Leu Arg Lys Xaa Pro Ala Ser Phe Cys Lys Pro Pro
1               5                   10                  15

Arg Arg Met Lys Trp Lys Lys
            20

<210> SEQ ID NO 22
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 22

Val Pro Xaa Xaa Leu Arg Lys Xaa Pro Glu Ser Phe Cys Lys Pro Pro
1               5                   10                  15

Arg Arg Met Lys Trp Lys Lys
            20

<210> SEQ ID NO 23
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 23

Val Pro Xaa Xaa Leu Lys Lys Xaa Pro Ala Ser Phe Cys Lys Pro Pro
1               5                   10                  15

Arg Arg Met Lys Trp Lys Lys
            20

<210> SEQ ID NO 24
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)

<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 24

Val Pro Xaa Xaa Leu Lys Arg Xaa Pro Ala Ser Phe Cys Lys Pro Pro
1               5                   10                  15

Arg Arg Met Lys Trp Lys Lys
            20

<210> SEQ ID NO 25
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 25

Ala Pro Xaa Xaa Leu Lys Lys Xaa Pro Asp Ser Phe Cys Lys Pro Pro
1               5                   10                  15

Arg Arg Met Lys Trp Lys Lys
            20

<210> SEQ ID NO 26
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (5)..(5)
<223> OTHER INFORMATION: Xaa=Nle
<220> FEATURE:
<221> NAME/KEY: misc_feature
<222> LOCATION: (8)..(8)
<223> OTHER INFORMATION: Xaa=Nle

<400> SEQUENCE: 26

Ala Pro Xaa Xaa Xaa Lys Lys Xaa Pro Asp Ser Phe Cys Lys Pro Pro
1               5                   10                  15

Arg Arg Met Lys Trp Lys Lys
            20

<210> SEQ ID NO 27
<211> LENGTH: 23
<212> TYPE: PRT
<213> ORGANISM: Artificial sequence

```
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 27

Val Pro Xaa Xaa Leu Lys Lys Xaa Pro Asp Ser Phe Cys Lys Pro Pro
1               5                   10                  15

Arg Arg Met Lys Trp Lys Lys
            20

<210> SEQ ID NO 28
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (5)..(5)
<223> OTHER INFORMATION: Xaa=Nle
<220> FEATURE:
<221> NAME/KEY: misc_feature
<222> LOCATION: (8)..(8)
<223> OTHER INFORMATION: Xaa=Nle

<400> SEQUENCE: 28

Val Pro Xaa Xaa Xaa Lys Lys Xaa Pro Asp Ser Phe Cys Lys Pro Pro
1               5                   10                  15

Arg Arg Met Lys Trp Lys Lys
            20

<210> SEQ ID NO 29
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (4)..(4)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 29

Val Pro Xaa Xaa Leu Lys Lys Xaa Pro Glu Ser Phe Cys Lys Pro Pro
1               5                   10                  15
```

```
<210> SEQ ID NO 30
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (8)..(8)
<223> OTHER INFORMATION: Xaa=Nle
<220> FEATURE:
<221> NAME/KEY: misc_feature
<222> LOCATION: (13)..(13)
<223> OTHER INFORMATION: Xaa=Hcy

<400> SEQUENCE: 30

Val Pro Xaa Cys Leu Lys Lys Xaa Pro Ala Ser Phe Xaa Lys Pro Pro
1               5                   10                  15

Arg Arg Met Lys Trp Lys Lys
            20

<210> SEQ ID NO 31
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=Hcy
<220> FEATURE:
<221> NAME/KEY: misc_feature
<222> LOCATION: (4)..(4)
<223> OTHER INFORMATION: Xaa=(3Cl-)F
<220> FEATURE:
<221> NAME/KEY: misc_feature
<222> LOCATION: (8)..(8)
<223> OTHER INFORMATION: Xaa=Nle

<400> SEQUENCE: 31

Val Pro Xaa Xaa Leu Lys Lys Xaa Pro Ala Ser Cys Phe Lys Pro Pro
1               5                   10                  15

Arg Arg Met Lys Trp Lys Lys
            20

<210> SEQ ID NO 32
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (5)..(5)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle
```

-continued

```
<400> SEQUENCE: 32

Val Pro Xaa Leu Xaa Lys Lys Xaa Pro Ala Ser Phe Lys Cys Pro Pro
1               5                   10                  15

Arg Arg Met Lys Trp Lys Lys
            20

<210> SEQ ID NO 33
<211> LENGTH: 23
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (7)..(7)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 33

Val Pro Xaa Leu Lys Lys Xaa Xaa Pro Ala Ser Phe Lys Pro Pro Cys
1               5                   10                  15

Arg Arg Met Lys Trp Lys Lys
            20

<210> SEQ ID NO 34
<211> LENGTH: 24
<212> TYPE: PRT
<213> ORGANISM: Artificial sequence
<220> FEATURE:
<223> OTHER INFORMATION: polypeptide
<220> FEATURE:
<221> NAME/KEY: MISC_FEATURE
<222> LOCATION: (18)..(24)
<223> OTHER INFORMATION: cell penetrating element

<400> SEQUENCE: 34

Val Pro Met Arg Leu Arg Lys Leu Pro Asp Ser Phe Phe Lys Pro Pro
1               5                   10                  15

Glu Arg Arg Met Lys Trp Lys Lys
            20

<210> SEQ ID NO 35
<211> LENGTH: 28
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (7)..(7)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 35
```

```
Val Pro Xaa Leu Lys Lys Xaa Xaa Pro Ala Ser Phe Lys Pro Pro Cys
1               5                   10                  15

Gly Arg Lys Lys Arg Arg Gln Arg Arg Lys Lys
            20                  25

<210> SEQ ID NO 36
<211> LENGTH: 28
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (7)..(7)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 36

Val Pro Xaa Leu Lys Lys Xaa Xaa Pro Ala Ser Phe Lys Pro Pro Cys
1               5                   10                  15

Gly Arg Lys Lys Arg Arg Gln Arg Arg Lys Lys
            20                  25

<210> SEQ ID NO 37
<211> LENGTH: 17
<212> TYPE: PRT
<213> ORGANISM: Artificial sequence
<220> FEATURE:
<223> OTHER INFORMATION: polypeptide
<220> FEATURE:
<221> NAME/KEY: misc_feature
<222> LOCATION: (3)..(3)
<223> OTHER INFORMATION: Xaa=(3Cl-)F
<220> FEATURE:
<221> NAME/KEY: misc_feature
<222> LOCATION: (7)..(7)
<223> OTHER INFORMATION: Xaa=Hcy
<220> FEATURE:
<221> NAME/KEY: misc_feature
<222> LOCATION: (8)..(8)
<223> OTHER INFORMATION: Xaa=Nle

<400> SEQUENCE: 37

Val Pro Xaa Leu Lys Lys Xaa Xaa Pro Ala Ser Phe Lys Pro Pro Cys
1               5                   10                  15

Lys
```